(12) United States Patent
Nallakrishnan

(10) Patent No.: US 9,504,459 B1
(45) Date of Patent: Nov. 29, 2016

(54) SURGICAL APPARATUS AND METHOD OF USE THEREOF

(71) Applicant: ASICO, LLC, Westmont, IL (US)

(72) Inventor: Ravi Nallakrishnan, Westmont, IL (US)

(73) Assignee: Ravi Nallakrishnan Revocable Trust, Willowbrook, IL (US)

( * ) Notice: Subject to any disclaimer, the term of this patent is extended or adjusted under 35 U.S.C. 154(b) by 0 days.

(21) Appl. No.: 14/833,996

(22) Filed: Aug. 24, 2015

Related U.S. Application Data

(60) Provisional application No. 62/186,976, filed on Jun. 30, 2015.

(51) Int. Cl.
*A61B 17/02* (2006.01)

(52) U.S. Cl.
CPC .................. *A61B 17/0231* (2013.01)

(58) Field of Classification Search
CPC ........................ A61B 17/0231; A61F 9/007
See application file for complete search history.

(56) References Cited

U.S. PATENT DOCUMENTS

| | | | | |
|---|---|---|---|---|
| 4,203,168 A * | 5/1980 | Rainin | ...................... | A61F 2/16 623/6.51 |
| 4,321,916 A | 3/1982 | McKee | | |
| 4,387,706 A * | 6/1983 | Glass | ................. | A61B 17/0231 600/208 |
| 4,782,820 A * | 11/1988 | Woods | ............... | A61B 17/0231 600/208 |
| 4,991,567 A * | 2/1991 | McCuen, II | ....... | A61B 17/0231 600/204 |
| 5,163,419 A * | 11/1992 | Goldman | .......... | A61B 17/0231 600/206 |
| 5,267,553 A * | 12/1993 | Graether | ............ | A61B 17/0231 600/236 |
| 5,299,564 A * | 4/1994 | Sabatino | ........... | A61B 17/0231 600/236 |
| 5,322,054 A * | 6/1994 | Graether | ............ | A61B 17/0231 269/303 |
| 5,374,272 A * | 12/1994 | Arpa | ....................... | A61F 9/007 600/236 |
| 5,951,565 A | 9/1999 | Freeman | | |
| 6,068,643 A * | 5/2000 | Milverton | ............... | A61F 9/007 606/107 |
| 6,200,336 B1 * | 3/2001 | Pavcnik | .................... | A61F 2/07 623/1.13 |
| 6,231,583 B1 * | 5/2001 | Lee | ......................... | A61F 9/007 606/151 |

(Continued)

FOREIGN PATENT DOCUMENTS

| | | |
|---|---|---|
| CA | 2902075 A1 | 9/2014 |
| WO | 2013059305 A1 | 4/2013 |
| WO | 2014132264 A1 | 9/2014 |

*Primary Examiner* — Christian Sevilla
(74) *Attorney, Agent, or Firm* — Wood, Phillips, Katz, Clark & Mortimer

(57) ABSTRACT

A surgical apparatus for use in assisting the performance of a procedure on an eye, the eye having a front and rear, a cornea, an iris defining a pupil, and a lens capsule behind the iris. The apparatus has a frame with a front and rear, a first portion and a second portion. The first frame portion has at least one iris engagement portion for being operatively connected to the iris to exert a pressure upon the iris that maintains the pupil in an enlarged state. The second frame portion has a curved edge configured to guide movement of an instrument in a curved path with the first frame portion operatively connected to an iris.

15 Claims, 18 Drawing Sheets

(56) References Cited

U.S. PATENT DOCUMENTS

| | | | | |
|---|---|---|---|---|
| 8,323,296 | B2 * | 12/2012 | Malyugin | A61B 17/0231 606/107 |
| 8,439,833 | B2 | 5/2013 | Christensen et al. | |
| D686,729 | S | 7/2013 | Christensen et al. | |
| 8,496,583 | B1 * | 7/2013 | Reynard | A61B 17/0231 600/235 |
| 8,852,091 | B2 | 10/2014 | Sussman et al. | |
| 8,900,136 | B2 * | 12/2014 | Cote | A61F 9/00736 600/208 |
| 9,089,397 | B2 | 7/2015 | Clarke | |
| 2003/0092970 | A1 * | 5/2003 | Lee | A61B 17/0231 600/236 |
| 2008/0108879 | A1 | 5/2008 | Brown | |
| 2008/0243139 | A1 * | 10/2008 | Dusek | A61B 17/0231 606/107 |
| 2008/0275461 | A1 * | 11/2008 | Nallakrishnan | A61F 9/0008 606/107 |
| 2012/0136322 | A1 | 5/2012 | Alster et al. | |
| 2012/0289786 | A1 * | 11/2012 | Dusek | A61B 17/0231 600/236 |
| 2013/0053860 | A1 | 2/2013 | Malyugin | |
| 2013/0096386 | A1 * | 4/2013 | Christensen | A61B 17/0231 600/206 |
| 2013/0131458 | A1 * | 5/2013 | Malyugin | A61B 1/32 600/236 |
| 2013/0267988 | A1 * | 10/2013 | Sussman | A61B 17/0231 606/198 |
| 2013/0331939 | A1 * | 12/2013 | Stevens | A61F 2/16 623/6.51 |
| 2014/0221759 | A1 | 8/2014 | Mackool et al. | |
| 2014/0378773 | A1 * | 12/2014 | Dykes | A61B 17/0293 600/208 |
| 2015/0080665 | A1 | 3/2015 | Cote et al. | |

* cited by examiner

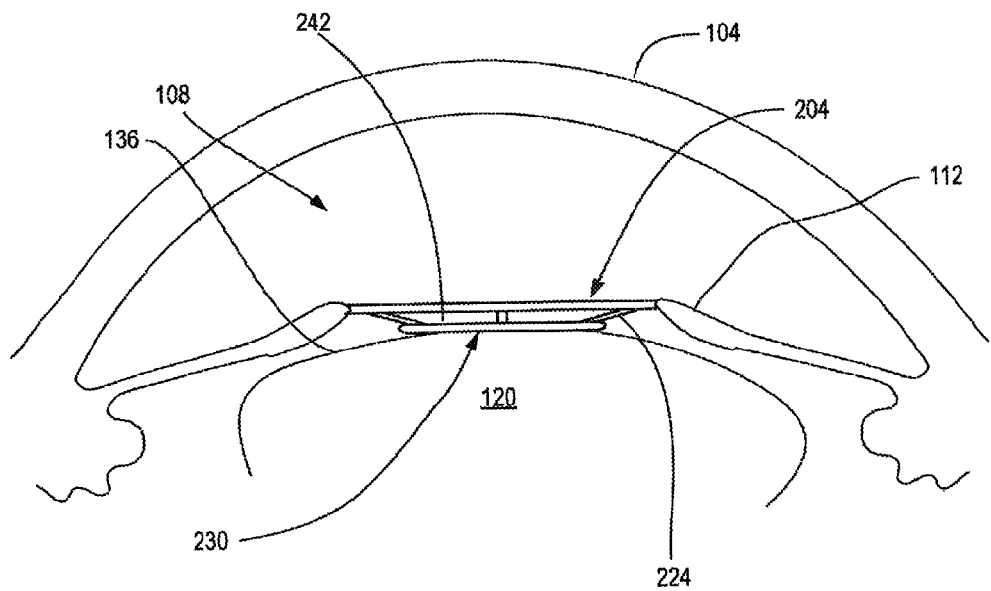
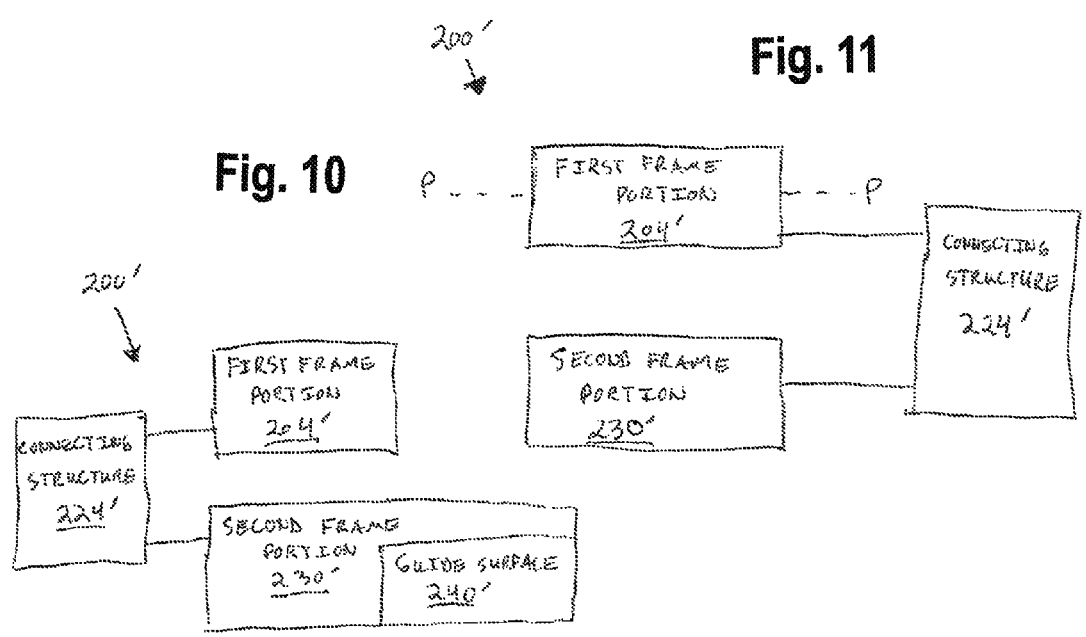

SURGICAL APPARATUS AND METHOD OF USE THEREOF

FIELD OF THE INVENTION

The present invention relates generally to the field of surgery, and more particularly to an apparatus for use during ophthalmic surgery.

BACKGROUND OF THE INVENTION AND TECHNICAL PROBLEMS POSED BY THE PRIOR ART

Removal of the lens in an eye is required by such physical conditions as cataracts, disease, or trauma to the eye. Typically, the removal of a lens is accomplished by making an opening in the anterior wall of the lens capsule, and then using surgical techniques such as phacoemulsification to fragment and remove the lens. Thereafter, an artificial intraocular lens (IOL) is inserted through the opening in the lens capsule to replace the damaged or diseased lens.

To make an opening in the lens capsule, a surgeon will first retract the iris, dilating the pupil, typically through chemical dilation. However, for some patients a mechanical iris retractor must be utilized to retract the iris, such as in the case of a small or damaged iris. The mechanical iris refractor may be injected through an incision in the anterior chamber of the eye. Once the iris is retracted and the anterior capsule wall is adequately exposed within an inner portion or aperture of the iris retractor, the surgeon will use surgical instruments such as forceps or a needle to puncture the anterior capsular wall, then grip the wall at the site of the puncture and tug or tear the wall, preferably in a circular pattern to remove a portion of the wall large enough and appropriately shaped to receive an artificial IOL.

The above-discussed procedure requires significant skill on the part of the surgeon. It is not uncommon to produce a jagged or uneven opening as the wall tears. A smooth edge surrounding the opening in the capsule is desirable to avoid problems with loose flaps or strips that may be snagged when the lens particles are aspirated after the lens has been emulsified.

It would be desirable to provide an improved surgical apparatus wherein the above-discussed problems could be eliminated, or at least substantially minimized.

It would further be desirable to provide an improved iris retractor that may be utilized for a variety of patients having differing pupil sizes.

Further, it would be beneficial if such an improved iris retractor could be manufactured without incurring excessive costs or expenses.

SUMMARY OF THE INVENTION

The inventor of the present invention has determined how to provide an inventive surgical apparatus for use in assisting the performance of a procedure on an eye, the eye having a front and rear, a cornea, an iris defining a pupil, and a lens capsule behind the iris. In one form, the apparatus has a frame having a front and rear, a first portion and a second portion. The first frame portion has at least one iris engagement portion for being operatively connected to an iris to exert a pressure upon the iris that maintains the pupil in an enlarged state. The second frame portion has a curved edge configured to guide movement of an instrument in a curved path with the first frame portion operatively connected to the iris.

In another form, the apparatus has a frame having a front and rear, a first portion and a second portion. The first frame portion is reconfigurable between a first starting state and a second operative state. The first frame portion is operatively connected to the iris and in the second operative state configured to exert a pressure upon the iris that maintains the pupil in an enlarged state. The frame is configured so that the second frame portion is urged rearwardly relative to the first frame portion as an incident of the first frame portion being changed from the first starting state into the second operative state.

BRIEF DESCRIPTION OF THE DRAWINGS

In the accompanying drawings forming part of the specification, in which like numerals are employed to designate like parts throughout the same:

FIG. 9 is a diagrammatic view of the apparatus shown in FIG. 2 operatively engaged with a human eye;

FIG. 10 is a diagrammatic view of an apparatus according to the present invention;

FIG. 11 is a diagrammatic view of another apparatus according to the present invention;

DETAILED DESCRIPTION OF THE DRAWINGS

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed.

Figure 1:
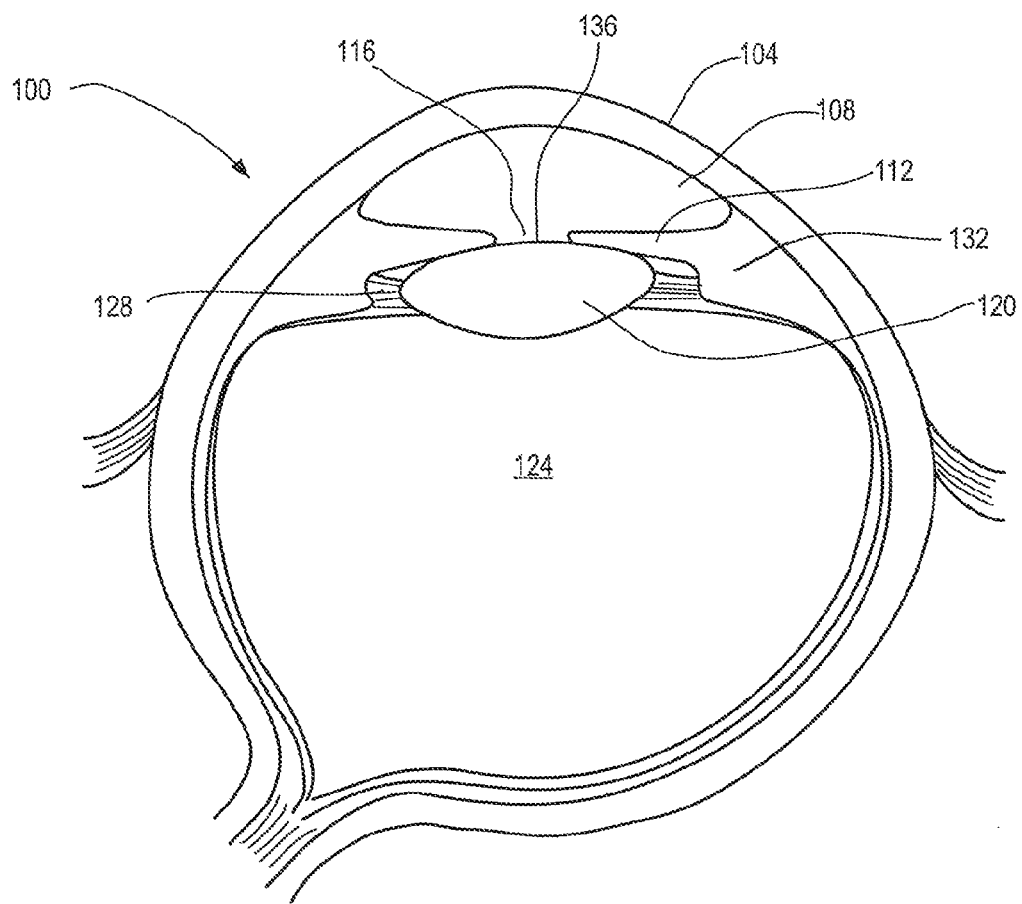
FIG. 1 is a diagrammatic, front-to-rear cross-sectional view through the center of a human eye.

Referring to FIG. 1, the numeral 100 identifies a longitudinal cross-sectional, diagrammatic view of a human eye showing the cornea 104, anterior chamber 108, iris 112 and pupil 116. Positioned behind the iris 112, and in line with the pupil 116, is the capsular bag 120, within which the lens resides. A posterior chamber 124 is located rearward of the capsular bag 120. A ciliary body 128 helps support capsular bag 120 through fiber-like zonules 132. Directions are utilized herein are made with reference to the eye 100. Outwardly or forwardly refers to the general direction moving from the posterior or rear portions of the eye (e.g., the posterior chamber 124) toward the anterior or front portions of the eye (e.g., the cornea 112).

Typically, when performing capsulorhexis, a surgeon creates an incision in the cornea 104 through which forceps are inserted and used to pierce the anterior portion or wall 136 of capsular bag 120 and to shear or tear it in a circular pattern to allow the damaged or diseased lens to be removed by phacoemulsification and, thereafter, the insertion of an IOL into capsular bag 120. To assist with performing capsulorhexis, the pupil is dilated by mechanically retracting the iris 112. Known methods for retracting the iris 112 involve insertion of collapsed rigid structures through the incision in the cornea 104, which are subsequently expanded into a deployed configuration whereby the iris 112 is pulled back from the center of the eye and the pupil 116 is dilated. Upon the removal of the anterior portion 136 of the capsule 120, the deployed structure may be re-collapsed and pulled from the eye through the incision in the cornea 104.

Figure 2:
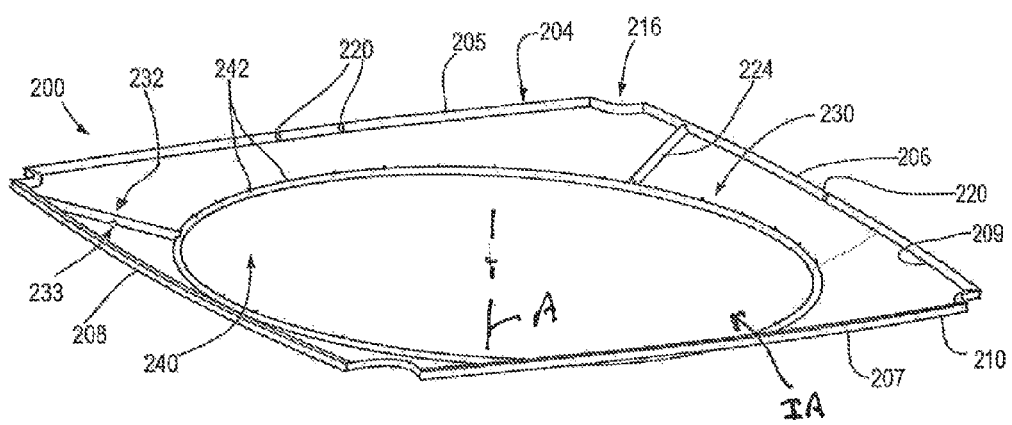
FIG. 2 is perspective view of a first embodiment of an apparatus according to the present invention.

Referring now to FIGS. 2-11, a first embodiment of a surgical apparatus, pupil expander, iris retractor, or simply refractor according to the present invention is denoted by numeral 200. In FIG. 2, the retractor 200 is generally shown in a deployed, second, or operative state that the retractor 200 may have within the pupil 116 (FIG. 8) so as to connect and retract the iris 112 (FIGS. 8 and 9) after having been collapsed (FIG. 7) and inserted through an incision in the cornea 104 (FIG. 9), as will be discussed in detail hereinafter. The retractor 200 is preferably injection molded or otherwise formed from a resilient material such as molded silicone, nylon, polypropylene, acrylic or polymethyl methacrylate (PMMA), wire, coated wire, etc. that may be collapsed for insertion through a small incision in the cornea 104, and which resiliently expands thereafter with sufficient rigidity to mechanically retract the iris 112. Various features of the retractor 200 may be punch cut or photoetched.

Figure 3:
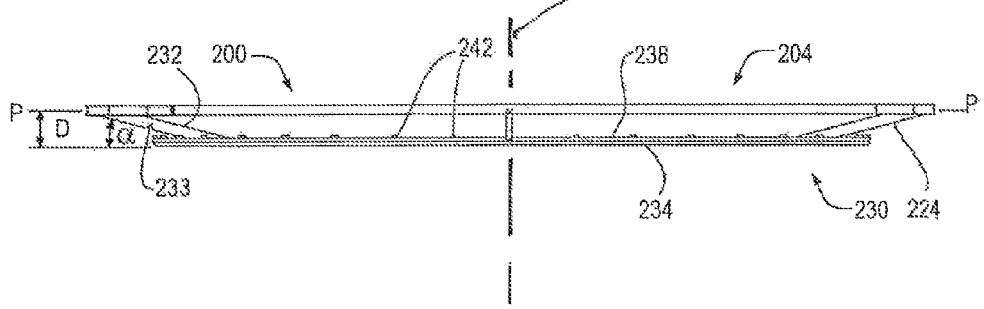
FIG. 3 is a side elevation view of the apparatus shown in FIG. 2.

Referring to FIG. 3, the refractor 200 is formed as a unitary frame having a first frame portion 204 that is generally polygonal in shape. The first frame portion 204 may have a variety of shapes, such as circular, three-sided polygon, more than four-sided polygon, or irregularly shaped or curved, etc., but is preferably at least nominally rectangular, defining four opposing segments or sides 205, 206, 207, and 208. Referring to FIG. 3, the first frame portion 204 generally resides in a horizontal plane P running therethrough. The terms "laterally inward" and "laterally outward", as used hereinafter, refer to directions generally within the plane P moving toward the geometric center of the retractor 200 and away from the geometric center of the retractor, respectively. The terms "forward" and "rearward", as used hereinafter, refer to the directions normal to the plane P.

Figure 4:
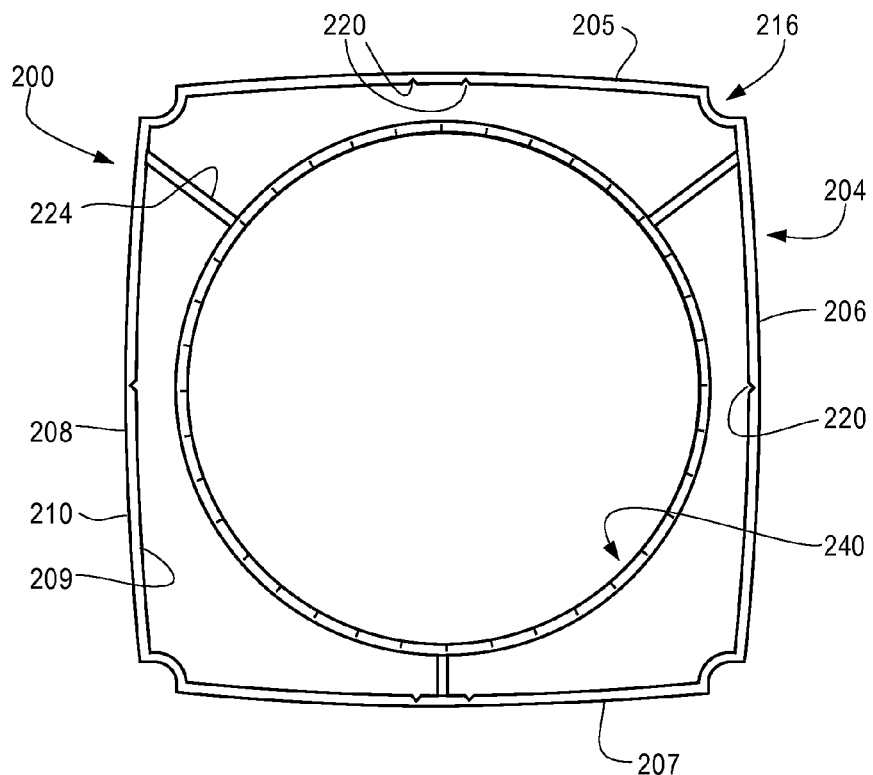
FIG. 4 is a top plan view of the apparatus shown in FIG. 2.
Figure 5:
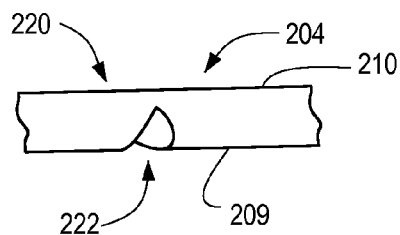
FIG. 5 is an enlarged partial, detailed view of a hinged portion of the apparatus shown in FIG. 2.
Figure 6:
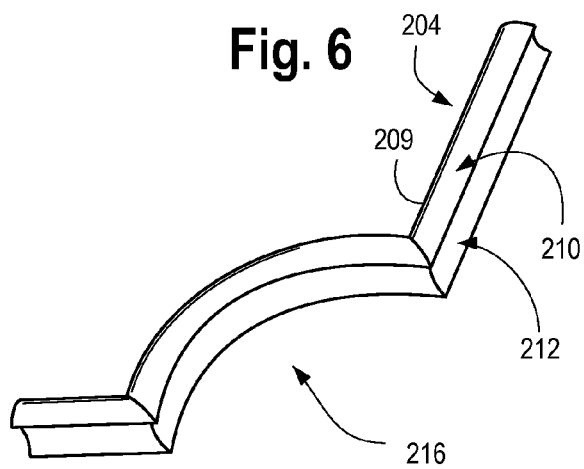
FIG. 6 is an enlarged partial, detailed view of an iris engagement portion of the apparatus shown in FIG. 2.
Figure 7:
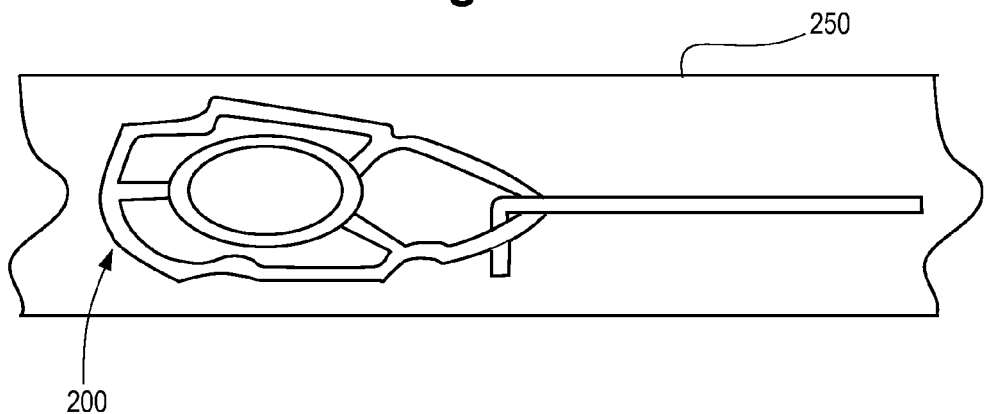
FIG. 7 is a perspective view of the apparatus shown in FIG. 2 in a collapsed configuration being loaded into an injector.

As best seen in FIGS. 4 and 5, the first frame portion 204 is provided with a laterally inward surface 209 and an opposing, laterally outward surface 210. The laterally outward surface 210 bounds a groove or channel 212 (FIG. 6) for accommodating or receiving a portion of the iris 112 (FIG. 9) so as to locate or position the retractor 200 generally within the center of the pupil 116 (FIG. 1), as will be discussed in detail hereinafter. The first frame portion 204 has four inverted corners or outwardly open iris engagement members 216, each defining a concave surface, that may alternatively be used to accommodate or receive the iris 112 (FIG. 8) by positioning one portion of each iris engagement member 216 above the iris 112 and one portion of each corner 112 below the iris 112 to locate the retractor 200 generally in the center of the pupil 116. In the broad concept of the invention, the first frame portion 204 need not have any channel 212 formed therein, and may have a fully circular, square, polygonal, or irregular cross-sectional shape. Furthermore, it will be understood that the first frame portion 204 may have any number of iris engagement portions sized and shaped to accommodate or receive a portion of the iris 112, and those portions may have the form of projections, inverted portions, channels, loops, coils, or any series of bends defining spaces configured for accommodating and receiving a portion of the iris 112, as will be discussed in detail hereinafter.

With reference to FIG. 5, the first frame portion 204 may be provided with a plurality of thinned regions, living hinges, or simply hinges 220. Each of the depicted hinges 220 is defined by a notch 222 in the exemplary first frame portion 204 to assist in bending of the iris retractor 200 into a collapsed starting state. As illustrated in FIG. 4, the retractor 200 has six hinges 220 located on the first frame portion 204; four hinges 220 are located on opposing sides 205 and 207 of the frame 204, while two hinges 220 are located on the other opposing sides 206 and 208 of the first frame portion 204. The hinges 220 are oriented on the first frame portion 204 such that the notches are located on the interior or laterally inward surface 209 to assist in the folding or bending of the first frame portion 204 generally within the plane P. It will be appreciated that the first frame portion 204 may be provided without any hinges 220 or that the hinges 220 may be located, oriented, or spaced differently on the first frame portion 204 to assist in other modes of collapsing or bending.

As can be seen in FIGS. 3 and 4, the retractor 200 has three struts or supports 224 that extend from the laterally inward surface 209 of the frame 204 to terminate in an instrument guide that makes up part of a second frame portion 230. The retractor 200 may be provided with only one support 224 or any number of supports 224 depending on the desired material, rigidity, and bending motion of the retractor 200. The supports 224 may also be provided with one or more thinned regions, living hinges, or simply hinges 232. Each of the depicted hinges 232 is defined by a notch 233 (FIG. 3) to assist in bending of the retractor 200 in a predetermined manner from a generally planar collapsed or as-manufactured configuration, for insertion into the eye, into a multi-planar deployed configuration wherein the second frame portion 230 is rearwardly spaced from the plane P and wherein the sides 205, 206, 207, 208 form a perimeter around an interior area. It will be appreciated that for some applications, the supports 224 may be provided without any hinges 232. Referring to FIG. 3, in the second operative state, the second frame portion 230 is rearwardly spaced from the first frame portion 204 a distance D between about 0.01 mm and about 0.20 mm. The supports 224 preferably extend from the first frame portion 204 to the second frame portion 230 at an angle α of about 1 to 30 degrees, with respect to the plane P.

Referring now to FIG. 3, the second frame portion 230 has a posterior or rear surface 234 for being located against or proximal to the lens capsule 120 (FIG. 9 only). The second frame portion 230 further has an anterior or forward surface 238 facing away from the capsule lens 120. The second frame portion 230 defines an inner aperture 240 (FIG. 4 only) to assist the surgeon in performing the capsulorhexis on the capsule 120, which will be discussed in greater detail herein. The second frame portion 230 preferably has a diameter of between about 4 and 8 millimeters, depending on the size of the patient's pupil. The forward surface 238 has a plurality of indicia or markings 242 for assisting the surgeon in making measurements of the eye, such as for measuring the amount of the capsule 120 being torn open. Preferably, the indicia are raised projections spaced every 5, 10, or 15 degrees around the forward surface 238. The indicia are preferably colored differently than the second frame portion 230 so as to have a greater visibility to the surgeon.

Operation of the retractor 200 will now be discussed. The retractor 200 is preferably manufactured or otherwise formed such that the first and second frame portions 204 and 230, respectively, reside within the plane P so as to define a first starting state. The retractor 200 may be manually bent or collapsed by a surgical instrument or the retractor 200 may be loaded into a needle 250 (FIG. 7) of a plunger type injector. It is a well-known ophthalmic surgical technique to fold iris retractors or IOLs to decrease their size to thereby minimize the size of the incision which must be made through the cornea 104 (FIG. 1) to allow the iris retractor or IOL to be inserted therethrough. The flexible material of the retractor 200, in addition to the hinges 220/232, aid the retractor 200 in collapsing so as to fit within the injector needle 250 and through the incision in the cornea 104. If the use of an injector is not desirable, then the retractor 200 may be folded or stored within a blister-type package or case and removed with forceps. Preferably, Kelman-McPherson style grooved forceps or straight forceps with a 15 degree curve could be utilized.

After an incision has been made through the cornea 104 (FIG. 1), such as by a scalpel, the folded or collapsed refractor 200 is injected or inserted through the incision and positioned within anterior chamber 108 (FIG. 1). The surgeon then positions the first frame portion 204 within the pupil 116 such that at least one of the channel 212 or the iris engagement members 216 receive a portion of the iris 112 (FIGS. 8 and 9) to retract the iris 112 and expand the pupil 116. In this operative state, pressure is exerted on the first frame portion 204, which in turn may bend or flex laterally inwardly depending on the material rigidity and the number, location, and/or size of the hinges 220/232. The bending of the first frame portion 204 assists the supports 224 in moving rearwardly away from the plane P such that the second frame portion 230 is also urged rearwardly with respect to the first frame portion 204. The second frame portion 230 then rests proximal to or against the anterior portion of the capsular bag 120 (FIG. 9).

The inventor has found that novel movement of the second frame portion 230 with respect to the first frame portion 204 allows for the retractor 200 to be more inexpensively and easily manufactured or formed in a generally planar configuration, and may be collapsed to easily fit through a relatively small incision in the cornea 104. Furthermore, the movement of the second frame portion 230 with respect to the first frame portion 204 allows for the physician to control the amount of rearward movement of the second frame portion 230 with respect to the first frame portion 204 based on the manner in which the physician operatively engages the iris 112 (FIGS. 8 and 9) with the first frame portion 204.

Once the second frame portion 230 is moved proximal to or against the capsular bag 220 (FIG. 9), the inner aperture 240 (FIG. 8) provides a circular perimeter within which the surgeon may evenly guide a surgical instrument to tear the anterior portion of the capsular bag 120. The second frame portion 230 helps to minimize or at least reduce the creation of irregular flaps or portions of the capsular bag 120 that typically are generated during capsulorhexis. Such flaps may become clogged in aspiration tools.

Figure 8:
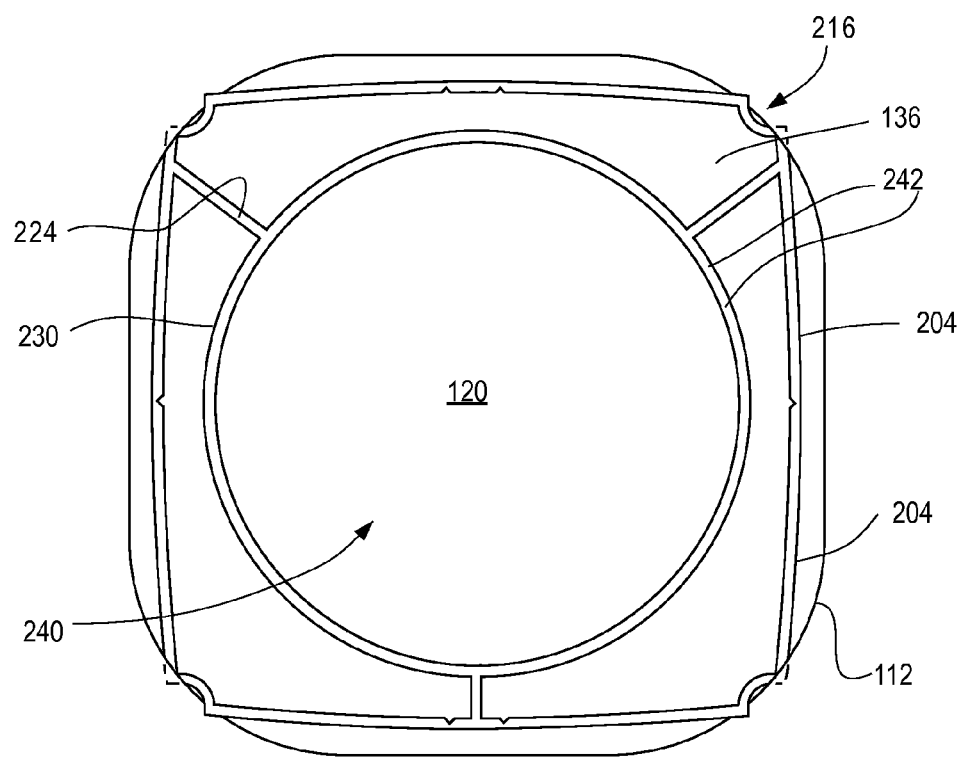
FIG. 8 is a top plan view of the apparatus shown in FIG. 2 operatively engaged with a human eye.

Referring now to FIG. 8, if the guide 230 of the iris retractor 200 is provided with indicia 242, then the surgeon may make measurements of the eye, such as determining the size and degree of the tear to be made in the capsule 120.

After capsulorhexis has been completed, and subsequent operations (e.g., phacoemulsification) have been completed, then the first frame portion 204 may be operatively disengaged from the iris 112. The disengagement of the iris 112 from the first frame portion 204 removes the pressures previously urging the second frame portion 230 rearwardly of the first frame portion 204, and the second frame portion 230 returns to reside generally within the plane P of the first frame portion 204. Thereafter, the retractor 200 may be collapsed by a surgical instrument, such as micro forceps, and pulled through the corneal incision and removed from the eye 100.

It will be appreciated that the retractor 200 could alternatively be manufactured such that the second frame portion 230 is spaced rearwardly from the first frame portion 204 in the starting state. In such an alternative manufactured configuration, the retractor 200 would similarly be folded or collapsed to fit through an incision in the cornea 104 and, due to the resiliency of the material of the retractor 200, would unfold or expand within the eye 100 into the operative state. The physician would then operatively engage the first frame portion 204 with the iris 112 and locate the second frame portion 230 against the capsular bag 120.

It will be appreciated that while various theories and explanations have been set forth herein with respect to how the frame portions of the retractor operate, there is no intention to be bound by such theories and explanations. Further it is intended that all structures falling within the scope of the appended claims are not to be otherwise excluded from the scope of the claims merely because the operation of such structures may not be accounted for by the explanations and theories presented herein.

Referring to FIG. 10, in generic depiction of the present invention, the iris retractor 200' has the basic components of a first frame portion 204' configured to operatively connect with the iris and which is connected to a second frame portion 230' having the form of a guide that defines a curved surface or aperture 240' for assisting with capsulorhexis or other surgical procedure on the eye 100. Connecting structure 224', including the supports 224, joins the frame portions 204' and 230'.

Referring to FIG. 11, in another generic depiction of the present invention, the iris retractor 200' has the basic components of a first frame portion 204' and second frame portion 230'. The first frame portion 204' has a starting state and is configured to be changed into an operative state wherein the first frame portion 204' engages the iris and the second frame portion 230' is urged rearwardly with respect to the first frame portion 204'. Connecting structure 224' joins the frame parts 204' and 230' to make this reconfiguration possible. It will be understood that the second frame portion 230' could have the form of a guide that defines an aperture 240' for assisting with capsulorhexis, but need not be limited to that particular function or structure.

The generic showing of the components in FIGS. 10 and 11 is intended to encompass not only the specific embodiments described herein, but variations thereof including virtually an unlimited number of variations of the components making up the retractor 200' and their interaction.

Figure 12:
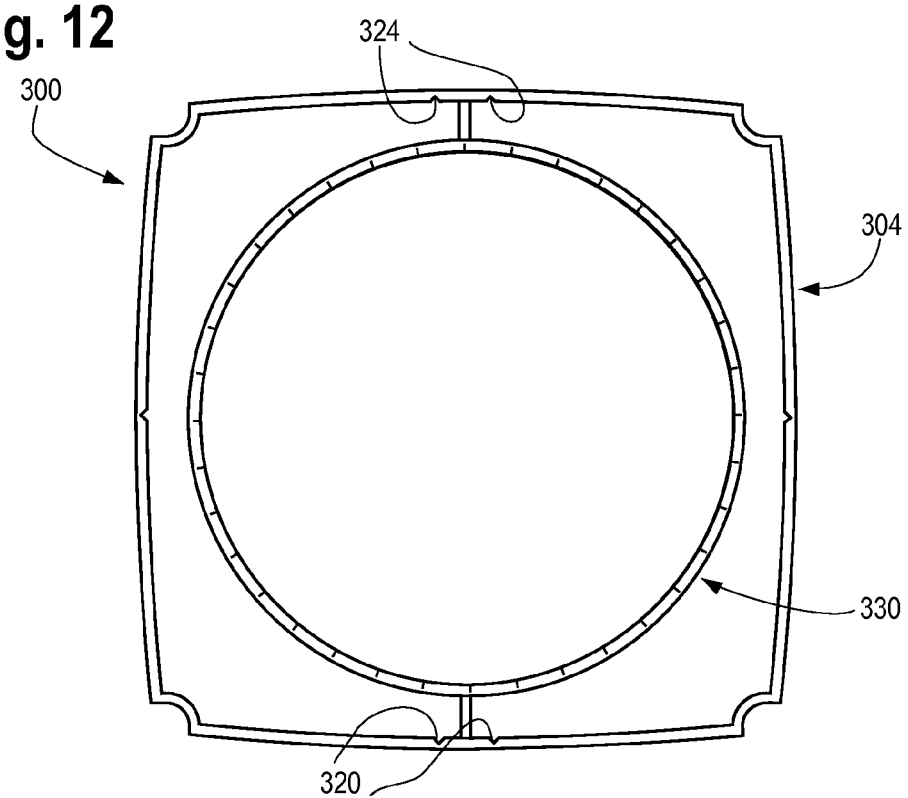
FIG. 12 is a top plan view of another embodiment of an apparatus according to the present invention.

Referring next to FIG. 12, another embodiment of an iris retractor or retractor 300 according to the present invention is illustrated. The retractor 300 functions in substantially the same manner as the retractor 200, with the exception that retractor 300 has a first frame portion 304 and guide or second frame portion 330 that are connected by only a pair of diametrically opposed supports 324. A plurality of hinges 320 are located along the first frame portion 304, to assist the iris retractor 300 in moving between the first starting state and the second operative state. Preferably, the hinges 320 are located adjacent each of the supports 324 to assist in urging the second frame portion 330 in the second operative state.

Figure 13:
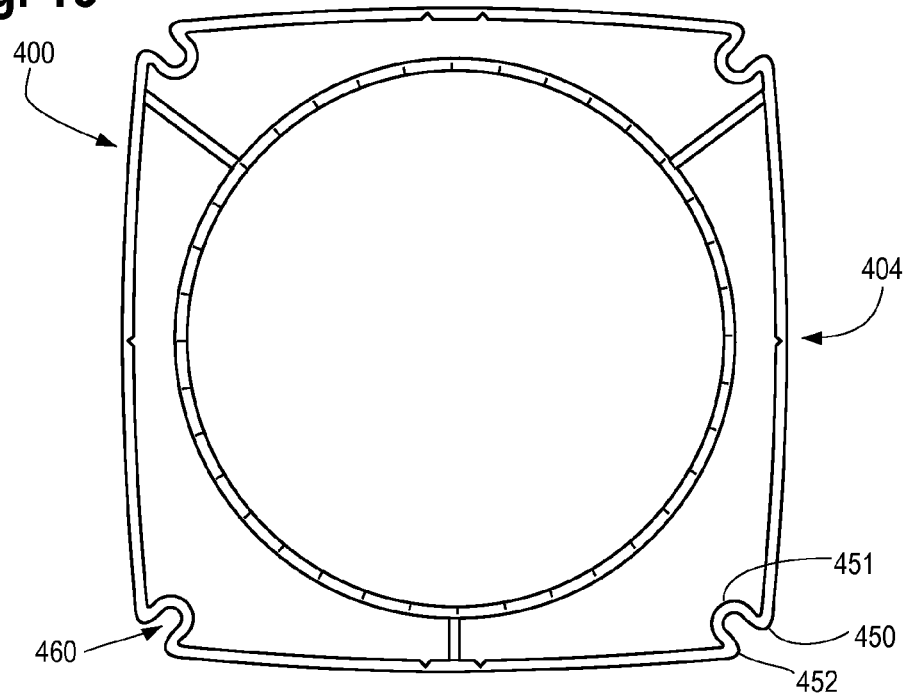
FIG. 13 is a top plan view of another embodiment of an apparatus according to the present invention.

Referring next to FIG. 13, another embodiment of an iris retractor or retractor 400 according to the present invention is illustrated. The retractor 400 functions in substantially the same manner as the retractor 200, with the exception that the retractor 400 has a first frame portion 404 wherein the iris engagement members have the form of a series of bends 450, 451, and 452 in each corner of the first frame portion 404. The bends 450, 451, and 452 define a channel or gap 460 for accommodating or receiving the iris 112 (not shown in FIG. 13). Positioning of the iris 112 within at least two gaps 460 functions to locate the first frame portion 404 in the center of the pupil 116 (not shown in FIG. 13).

Figure 14:
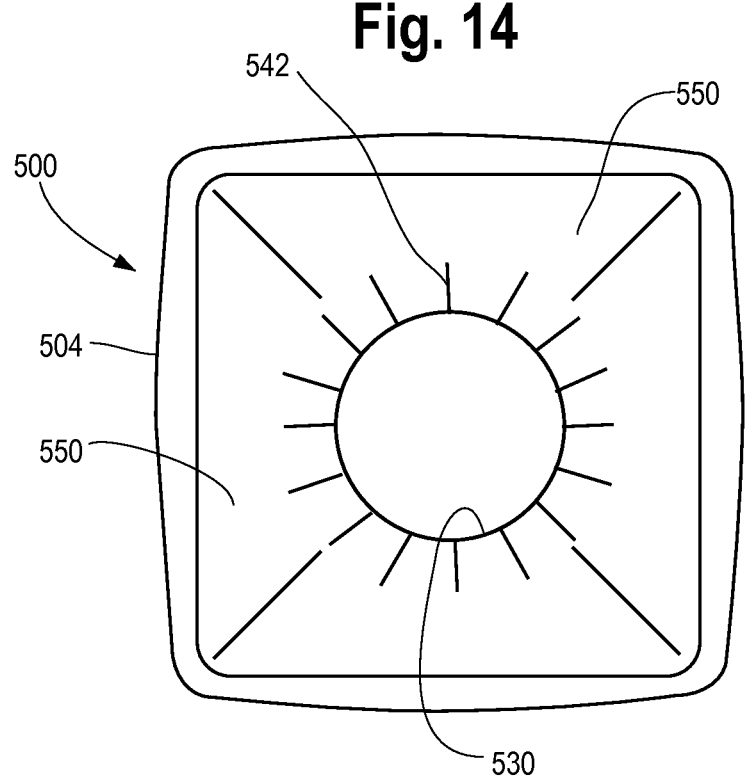
FIG. 14 is a top plan view of another embodiment of an apparatus according to the present invention.
Figure 15:
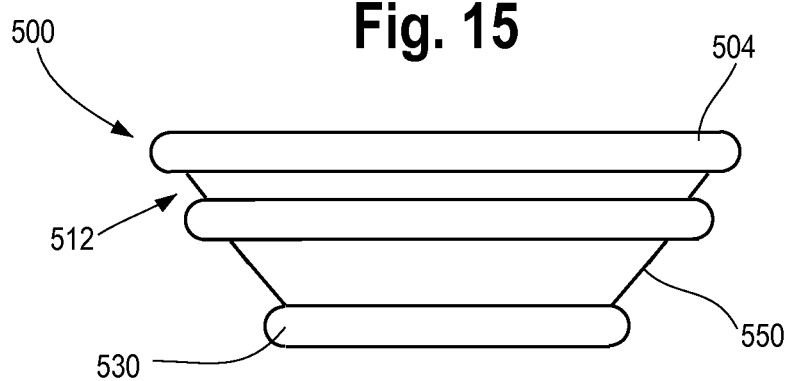
FIG. 15 is side elevation of the apparatus shown in FIG. 14.

Referring next to FIGS. 14 and 15, another embodiment of an iris retractor or retractor 500 according to the present invention is illustrated. The retractor 500 functions in substantially the same manner as the retractor 200, with the exception that the retractor 500 has a first frame portion 504 connected to a guide or second frame portion 530 by a unitary skirt 550. The skirt 550 is generally thinner or more flexible than the second frame portion 504 to assist the retractor 500 in moving between the starting state and the operative state. The retractor 500 may be provided with an annular channel 512 (FIG. 15) for operatively receiving a portion of the iris 112 (not illustrated in FIG. 15) to locate the retractor 500 within the eye. The channel could alternatively be located on a laterally outward surface of the frame, or no channel could be provided at all if the frame is provided with other means for engaging the iris as discussed herein.

Figure 16:
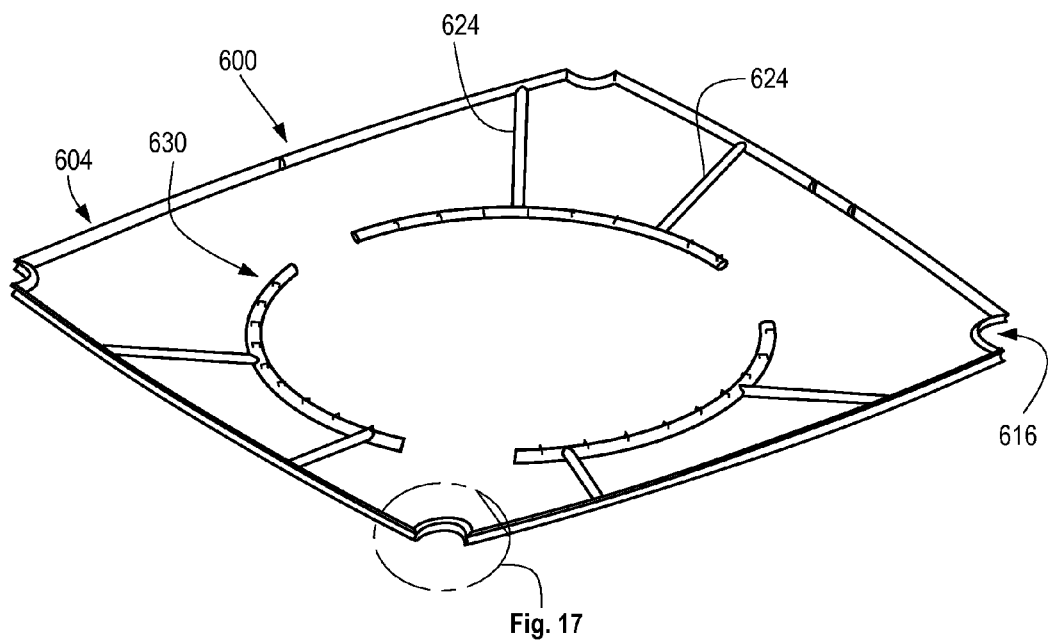
FIG. 16 is a perspective view of another embodiment of an apparatus according to the present invention.
Figure 17:
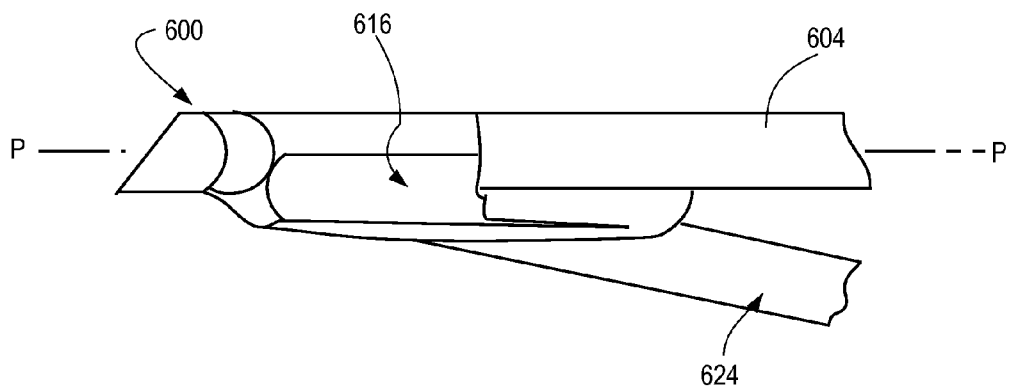
FIG. 17 is an enlarged, side elevation view of the circled area denoted as "FIG. 17", in FIG. 16.

Another embodiment of an iris retractor or retractor 600 according to the present invention is illustrated in FIGS. 16 and 17. The retractor 600 functions in substantially the same manner as the retractor 200, in that the retractor 600 has a first frame portion 604 with a plurality of inverted corners or outwardly open iris engagement members 616 for accommodating for receiving the iris 112 (not illustrated in FIGS. 16 and 17), structural supports 624 terminating in a guide or second frame portion 630 (FIG. 16). However, the retractor 600 has a discontinuous or segmented second frame portion 630 with each segment connected to the first frame portion 604 by a pair of supports 624. The segmentation of the second frame portion 630 may be constructed to be more flexible and configurable in a collapsed configuration for being inserted into the eye, compared to the iris retractor 200.

Referring to FIG. 17, iris engagement members 616 each extends rearwardly from the plane P defined by the first frame portion 604. It will be noted that such out-of-plane extension of the iris engagement members 616 may be provided on any of the embodiments of the retractor disclosed herein in lieu of a substantially planar (generally residing within the plane P) bend, recess, inverted corner, or other mechanism for gripping the iris 112. Some of the outwardly open iris engagement members 616 may extend in a first direction away from the plane P, while other outwardly open iris engagement members 616 may extend in a second direction away from plane P to engage the iris 112. Preferably, two outwardly open iris engagement members 616 at opposite corners would extend in the same direction out of the plane P, while the other two outwardly open iris engagement members 616 would extend in the opposite direction out of the plane P to balance the forces symmetrically between the iris 112 and the retractor 600.

Figure 18:
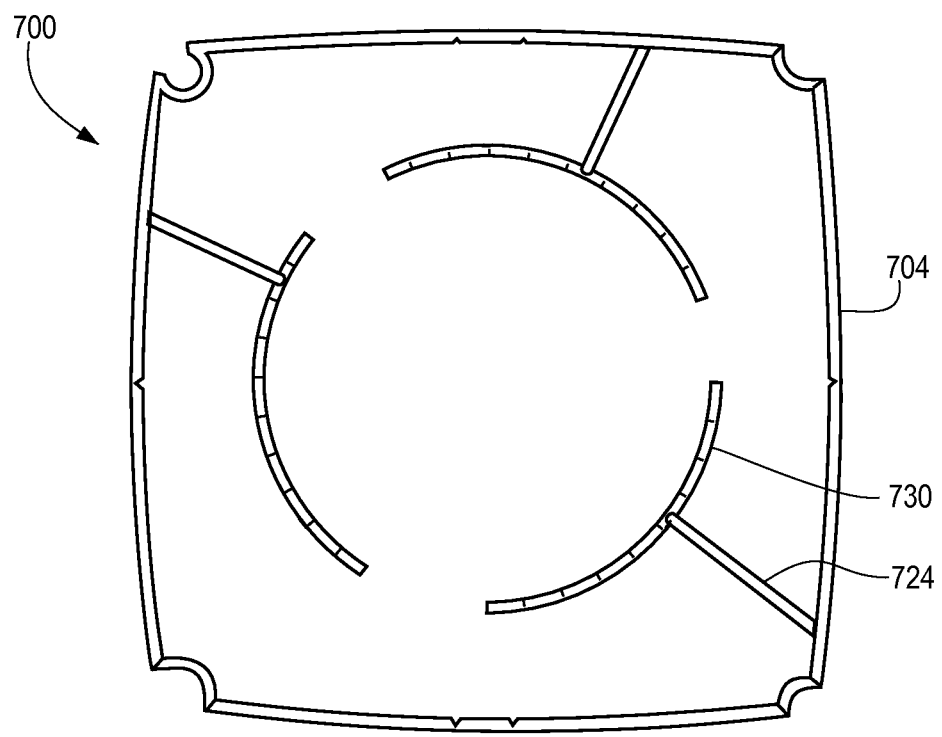
FIG. 18 is a top plan view of another embodiment of an apparatus according to the present invention.

Referring to FIG. 18, another embodiment of an iris retractor or retractor 700 according to the present invention is illustrated. The retractor 700 functions similarly to the iris retractor 600, with the exception that the retractor 700 has a first frame portion 704 that is connected to each segment of a guide or second frame portion 730 by only a single support 724. The retractor 700 may be constructed to be more easily configurable into, and out of, a collapsed configuration, when compared to the retractor 600.

Figure 19:
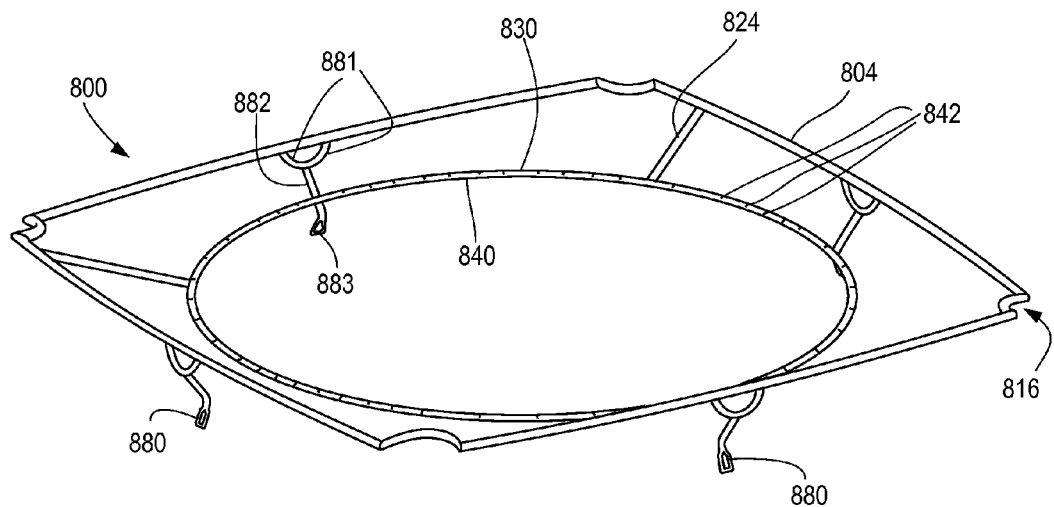
FIG. 19 is a perspective view of another embodiment of an apparatus according to the present invention.
Figure 20:
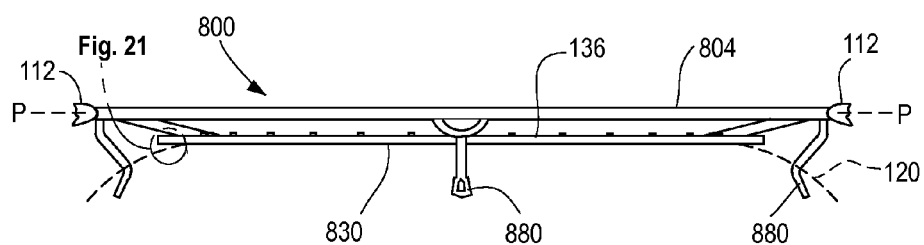
FIG. 20 is a side elevation view of the apparatus shown in FIG. 19.

Referring now to FIGS. 19-23, another embodiment of an iris retractor or retractor is shown and referenced by numeral 800. The retractor 800 functions similarly to the retractor 200, in that the retractor 800 has a first frame portion 804 that generally resides within a plane P, outwardly open corners or iris engagement members 816, supports 824, and a guide 830 defining an aperture 840 and is provided with indicia 842. The retractor 800 differs in that the first frame portion 804 has a plurality of projections, hooks, or capsule engagement members 880 extending therefrom. The capsule engagement members 880 serve to engage or lift the capsule 120 (FIG. 20) in the anterior direction after the capsulorhexis has been performed so as to stabilize the capsule 120 prior to phacoemulsification of the lens. The capsule engagement members 880 are preferably formed to reside generally within the plane P in the as-manufactured starting state, and then may be urged away the first frame portion 804 when the first frame portion 804 is pressured by the iris 112. Thus the capsule engagement members 880 may be considered as being, or being part of, a second frame portion. The capsule engagement members 880 preferably have the form of a pair of short legs 881 (FIG. 19) that join at a central, elongate body 882 (FIG. 19) that terminates in a generally triangular loop 883 (FIG. 19). It will be appreciated that the capsule engagement members 880 may terminate in other configurations such as discrete projections, or loops of a polygonal, circular, or irregular shape.

Figure 21:
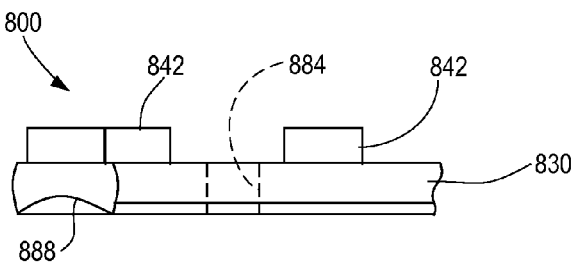
FIG. 21 is an enlarged view of the circled area denoted as "FIG. 21", in FIG. 20.
Figure 22:
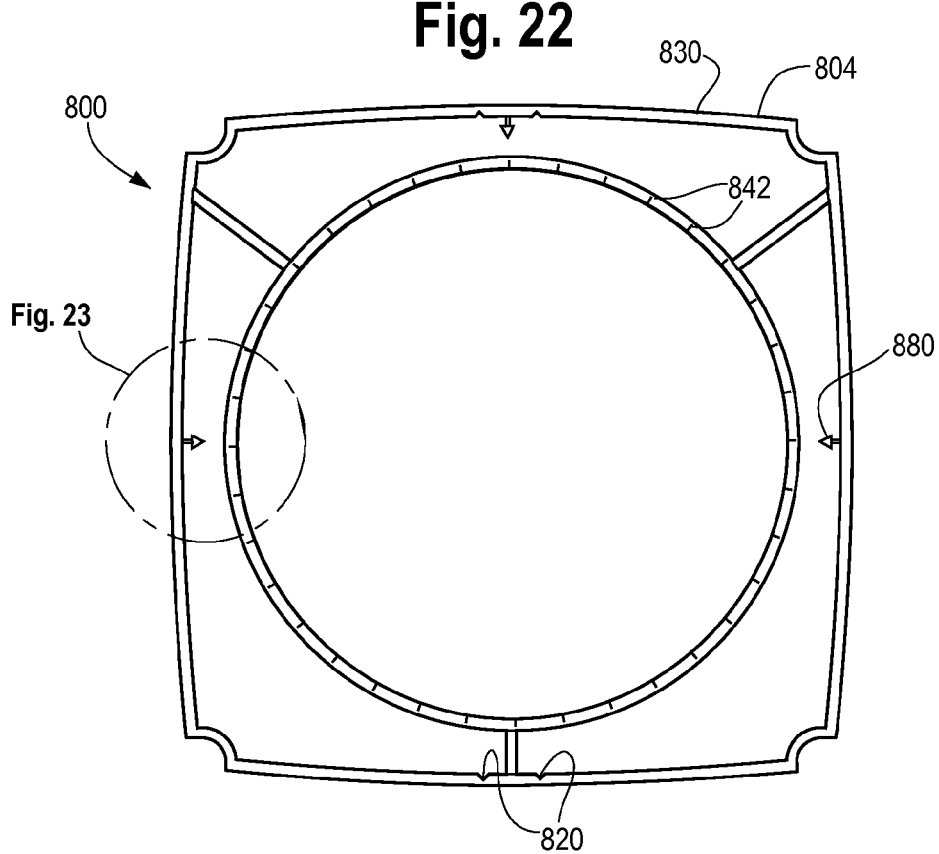
FIG. 22 is a top plan view of the apparatus shown in FIG. 19.
Figure 23:
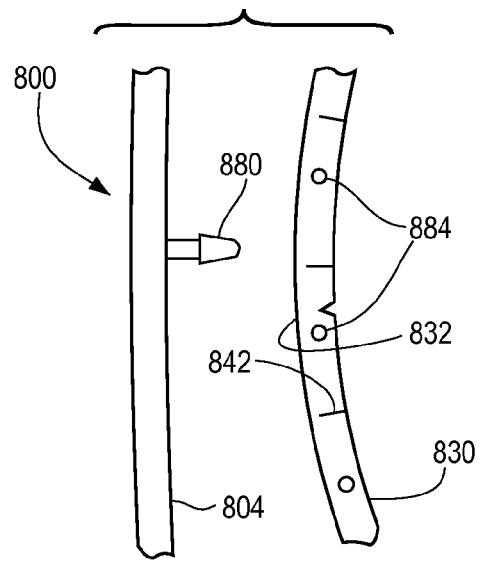
FIG. 23 is an enlarged view of the circled area denoted as "FIG. 23", in FIG. 22.
Figure 24:
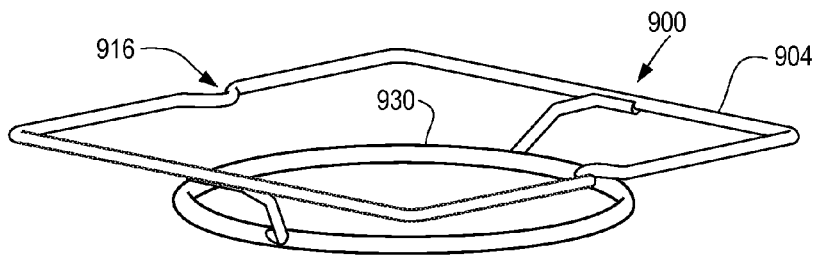
FIG. 24 is a perspective view of another embodiment of an apparatus according to the present invention.
Figure 25:
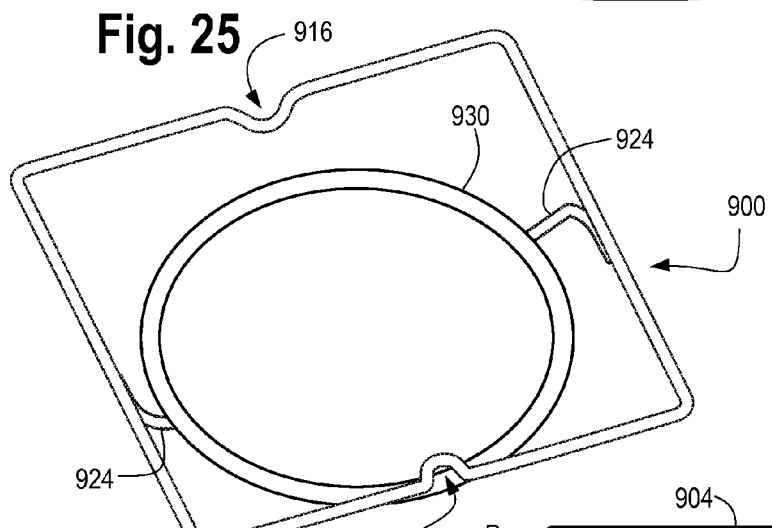
FIG. 25 is another perspective view of the apparatus shown in FIG. 24.
Figure 27:
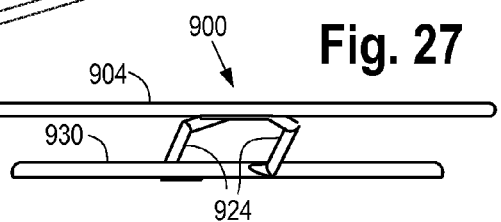
FIG. 27 is a side elevation view of the apparatus shown in FIG. 24.
Figure 26:
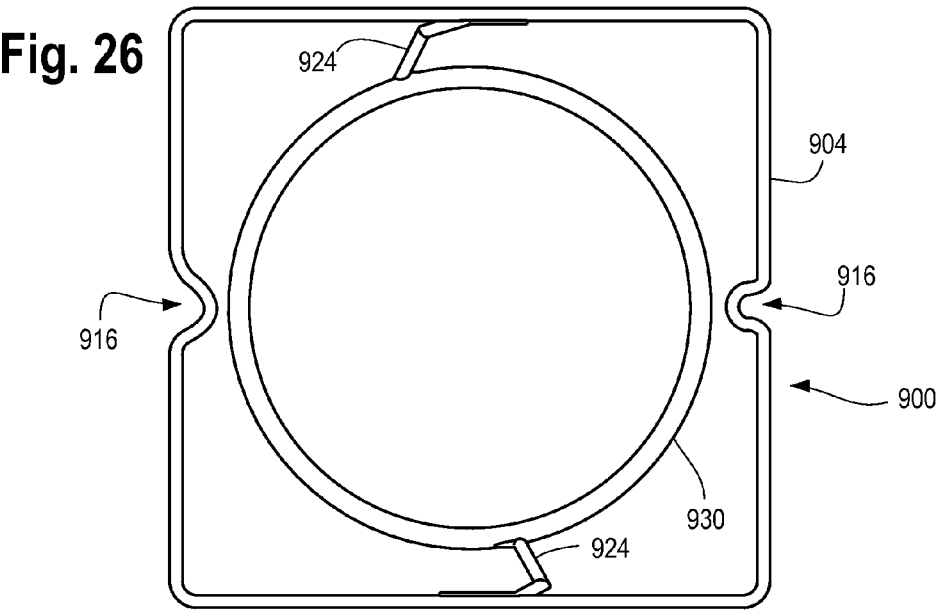
FIG. 26 is a top plan view of the apparatus shown in FIG. 24.

Referring next to FIGS. 21 and 23, the guide 830 is depicted as having a plurality of through holes or apertures 884 to allow fluid on or near the anterior surface 136 of the capsule 120 (not illustrated in FIGS. 21 and 23) to evacuate when the guide 830 is brought into contact with the anterior surface 136. It is believed that provision of the apertures 884 will create a significant capillary action of fluid through the apertures 884 to improve adherence of the guide 830 against the capsule 120. Referring to FIG. 21 only, the rear or posterior portion of the guide 830 that contacts the surface of the capsule 120 may also be provided with one or more recesses or grooves 888 to increase the surface area in contact with the surface of the capsule 120 and thus adhesion of the guide 830 to the surface of the capsule 120. It will be understood that in any of the embodiments of the iris retractor disclosed herein, the guide may be provided with one or more similar apertures and/or grooves.

Referring next to FIGS. 24-27, another embodiment of an iris retractor or retractor 900 according to the present invention is illustrated. The retractor 900 functions in a similar manner as the first embodiment of the retractor 200, in that the retractor 900 has a first frame portion 904 provided with a plurality of bends or outwardly open iris engagement members 916 for accommodating a portion of the iris 112 (not illustrated in FIGS. 24-27), and a plurality of supports 924 extending from the first frame portion 904 which terminate in a guide or second frame portion 930. The retractor 900 further has an as-manufactured first starting state and an operative state wherein when the frame portion 904 is pressured by the iris 112, then the second frame portion 930 is urged rearwardly away from the first frame portion 904. However, unlike the movement of the retractor 200, the movement of the second frame portion 930 of the refractor 900 into the operative state occurs in a more telescopic or torsional movement. The substantially arcuate shape and location of the supports 924 are believed to provide this telescopic or torsional/spiral reconfiguration. Alternatively, the supports could be made to have an elbow or L-shape so as to provide a lever-like action when rotating out of the plane of the first frame portion 904. Furthermore, the supports could be positioned between the first frame portion 904 and the second frame portion 930 such that they provide for a crossing, accordion-like telescopic movement of the second frame portion 930 with respect to the first frame portion 904.

Figure 28:
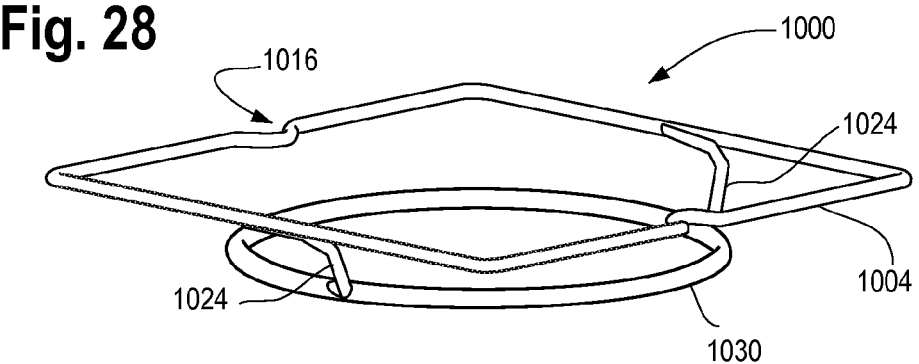
FIG. 28 is a perspective view of another embodiment of an apparatus according to the present invention.
Figure 29:
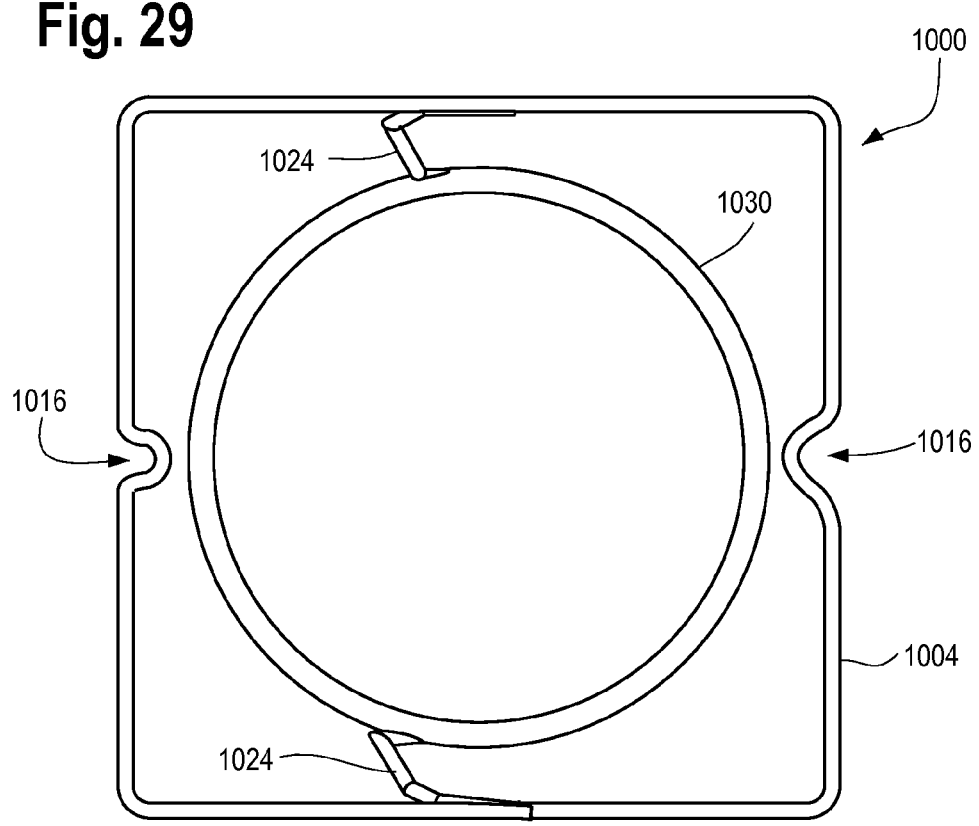
FIG. 29 is a top plan view of the apparatus shown in FIG. 28.
Figure 30:
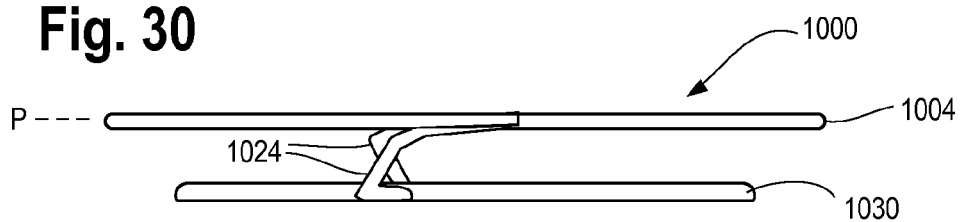
FIG. 30 is a side elevation view of the apparatus shown in FIG. 28.

Referring next to FIGS. 28-30, another embodiment of an iris retractor or retractor 1000 is illustrated. The retractor 1000 functions in a similar manner as the refractor 900, in that the retractor 1000 has a first frame portion 1004 provided with a plurality of bends or outwardly open iris engagement members 1016 for accommodating a portion of the iris 112 (not illustrated in FIGS. 28-30), and a plurality of substantially arcuate supports 1024 extending therefrom, each of which terminates at a guide or second frame portion 1030. The retractor 1000 further has an as-manufactured starting state and an operative state wherein when the first frame portion 1004 is pressured by the iris 112, the second frame portion 1030 is urged rearwardly away from the first frame portion 1004. However, unlike the movement of the retractor 900, the movement of the second frame portion 1030 of the retractor 1000 is in a more arcuate, rotational motion (rotating rearward away from a plane P in which the first frame portion 1004 resides). The alignment of the substantially arcuate supports 924 is believed to provide this unique movement of the second frame portion 1030.

Figure 31:
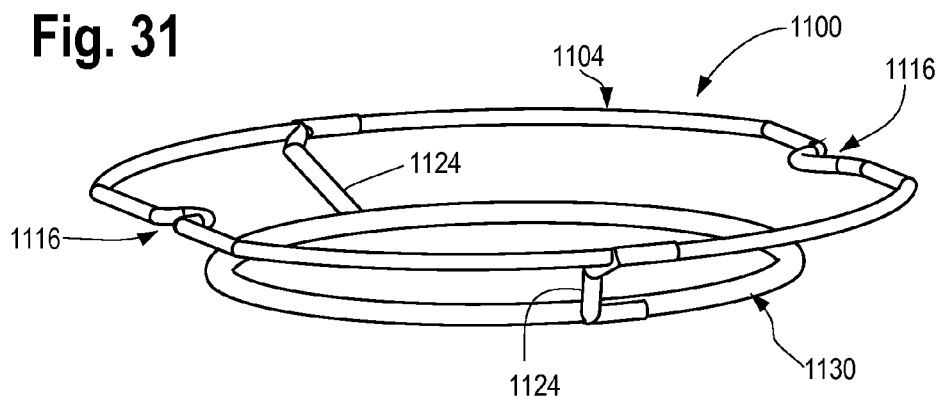
FIG. 31 is a perspective view of another embodiment of an apparatus according to the present invention.
Figure 32:
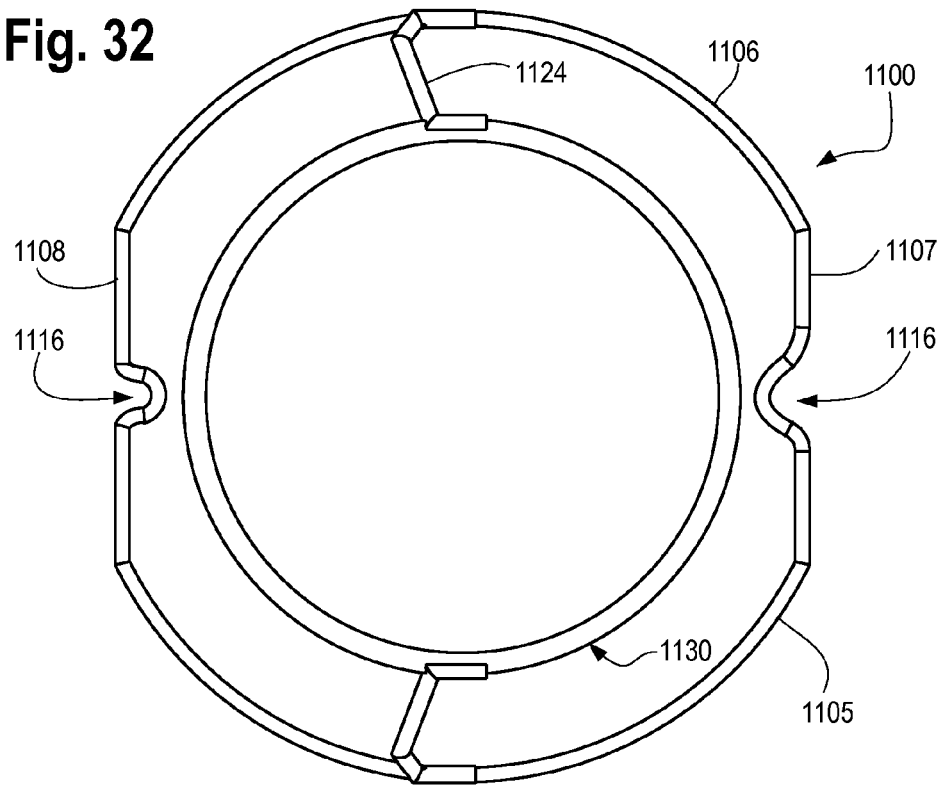
FIG. 32 is a top plan view of the apparatus shown in FIG. 31.
Figure 33:
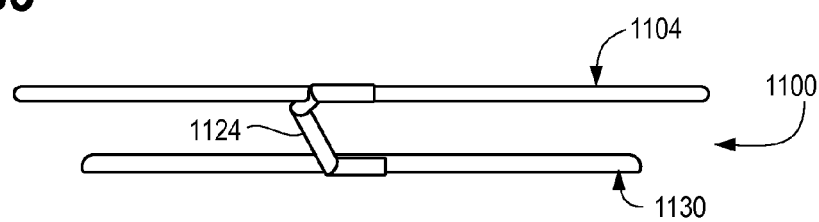
FIG. 33 is a side elevation view of the apparatus shown in FIG. 31.

Referring next to FIGS. 31-33, another embodiment of an iris retractor or retractor 1100 is illustrated. The retractor 1100 functions in a similar manner as the refractor 1000, in that the retractor 1100 has a first frame portion 1104 provided with a plurality of bends or outwardly open iris engagement members 1116 for accommodating a portion of the iris 112 (not illustrated in FIGS. 31-33), and a plurality of substantially arcuate supports 1124 extending therefrom and which terminate in a guide or second frame portion 1130. The retractor 1100 further has an as-manufactured starting state and a operative state wherein when the first frame portion 1104 is pressured by the iris 112, the second frame portion 1130 is urged rearwardly away from the first frame portion 1104. However, the first frame portion 1104 has opposing arcuate sides 1105 and 1106, respectively, from which the supports 1124 extend. Furthermore, the first frame portion 1104 has opposing substantially flat sides 1107 and 1108, respectively, on which the outwardly open iris engagement members 1116 are formed. The differing shape of the first frame portion 1104 is believed to provide a desirable movement of the second frame portion 1130 with respect to the first frame portion.

Figure 34:
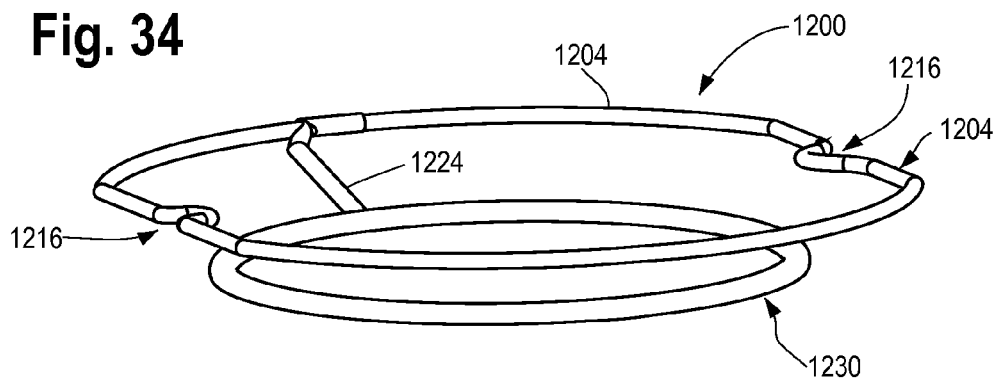
FIG. 34 is a perspective view of another embodiment of an apparatus according to the present invention.
Figure 35:
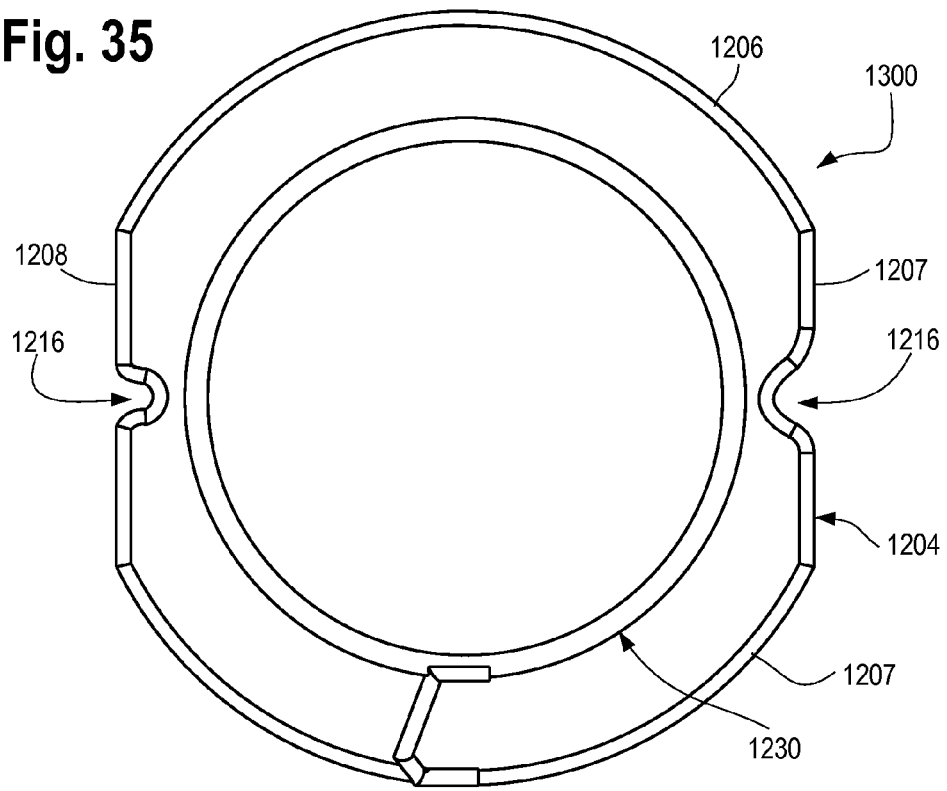
FIG. 35 is a top plan view of the apparatus shown in FIG. 34.
Figure 36:
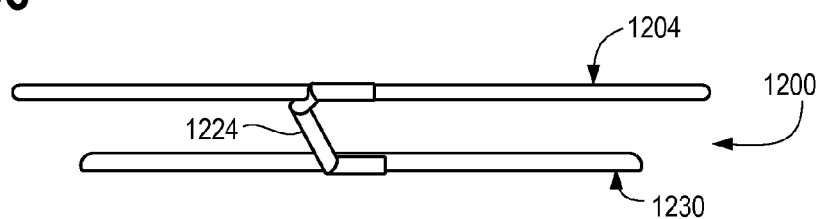
FIG. 36 is a side elevation view of the apparatus shown in FIG. 34.

Another embodiment of an iris retractor or retractor 1200 according to the present invention is illustrated in FIGS. 34-36. The retractor 1200 functions in a similar manner to the retractor 1100 in that the retractor 1200 has a first frame portion 1204 provided with a plurality of bends or outwardly open iris engagement members 1216 for accommodating a portion of the iris 112 (not illustrated in FIGS. 34-36), and a substantially arcuate support 1224 extending therefrom and which terminates in a guide or second frame portion 1230. The retractor 1200 further has an as-manufactured starting state and an operative state wherein when the first frame portion 1204 is pressured by the iris 112, the second frame portion 1230 is urged rearwardly away from the first frame portion 1204. The first frame portion 1204 has opposing arcuate sides 1205 and 1206, respectively, and has opposing substantially flat sides 1107 and 1108, respectively, on which the outwardly open iris engagement members 1116 are formed. However, the retractor 1200 is only provided with a single support 1224 which may facilitate manufacture of the retractor 1200 and enhance the flexibility of the retractor 1200 as it moves between the starting state and a operative state.

Figure 37:
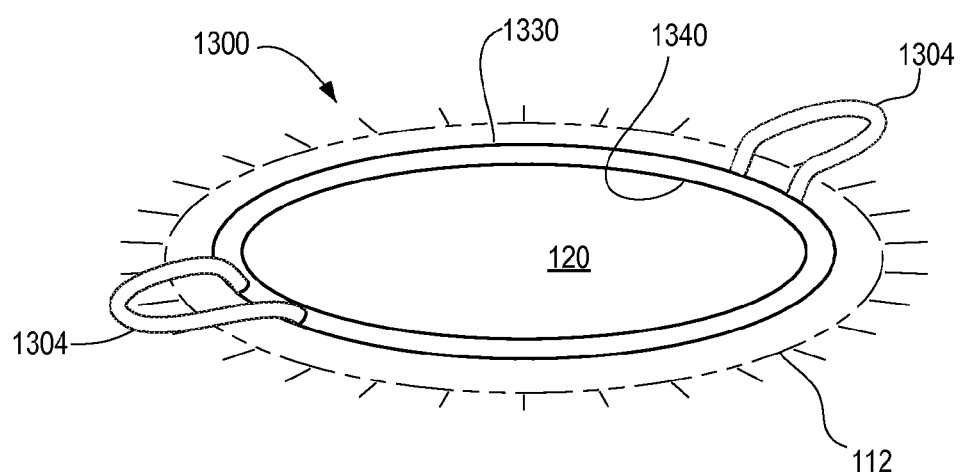
FIG. 37 is a perspective view of another embodiment of an apparatus according to the present invention operatively engaged with an iris of a human eye.
Figure 38:
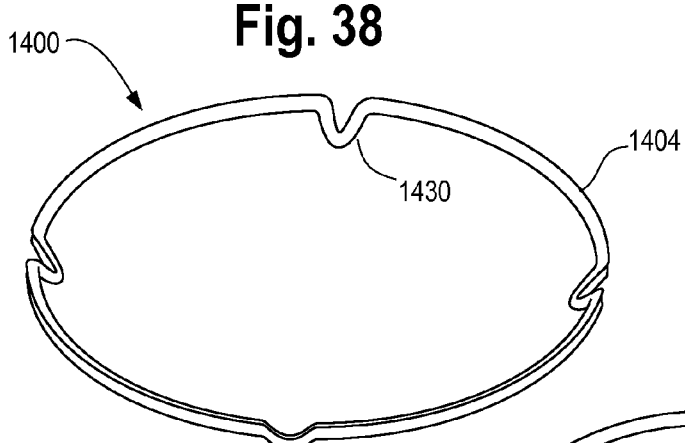
FIG. 38 is a perspective view of another embodiment of an apparatus according to the present invention.
Figure 39:
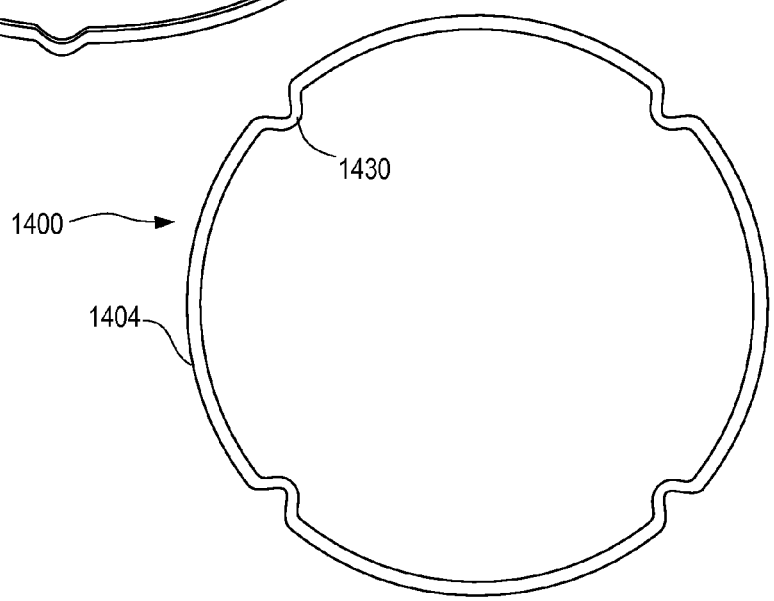
FIG. 39 is a top plan view of the apparatus shown in FIG. 38.
Figure 40:
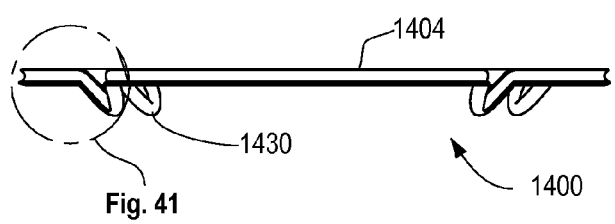
FIG. 40 is a side elevation view of the apparatus shown in FIG. 39.
Figure 41:
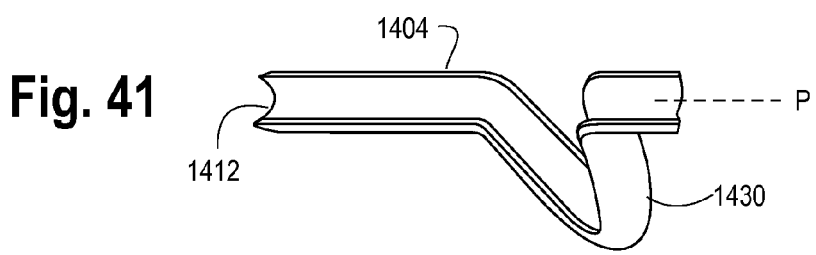
FIG. 41 is an enlarged view of the circled area denoted as "FIG. 41" in FIG. 40.

Referring next to FIG. 37, another embodiment of an iris retractor or retractor of the present invention is shown and referenced by numeral 1300. The retractor 1300 functions similarly to the first embodiment of the retractor 200 to the extent that the retractor 1300 has a first frame portion 1304 for exerting a pressure against the leading edge of the iris 112, and which is connected to a guide or second frame portion 1330 that defines an aperture 1340 for assisting with capsulorhexis. The retractor 1300 differs from the retractor 200 in that the first frame portion 1304 has the form of two relatively rigid projections or loops that are configured to retract the iris 112 without damaging the iris 112. Depending on the material rigidity of the first frame portion 1304, the pressure of the iris 112 against the first frame portion 1304 may urge the second frame portion 1330 to move rearwardly. The retractor 1300 might be made to be even more flexible and easily configurable in a collapsed configuration for being inserted into the eye, compared to the first illustrated embodiment of the iris retractor 200.

Figure 42:
FIG. 42 is a side elevation view of another embodiment of an apparatus according to the present invention.
Figure 43:
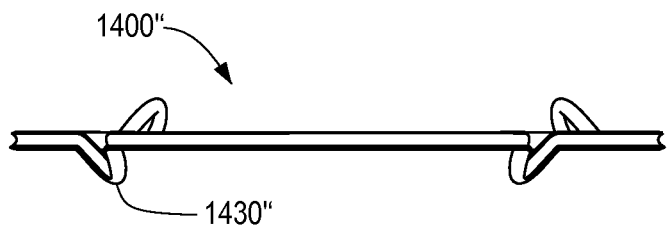
FIG. 43 is a side elevation view of another embodiment of an apparatus according to the present invention.
Figure 44:
FIG. 44 is a side elevation view of another embodiment of an apparatus according to the present invention.

Referring next to FIGS. 38-41, another embodiment of an iris retractor or retractor of the present invention is shown and referenced by numeral 1400. The retractor 1400 functions similarly to the first embodiment of the retractor 200 to the extent that the retractor 1400 has a first frame portion 1404 for exerting a pressure against the leading edge of the iris 112 (not illustrated in FIGS. 38-41). Specifically, with reference to FIG. 41, the frame 1404 has a channel 1412 for receiving the iris 112. The retractor 1400 differs from the retractor 200 in that the first frame portion 1404 has four rearwardly-extending projections defining a second frame portion 1430 for resting upon the anterior surface, or within a torn portion of, the capsule 120 (FIG. 1) for stabilizing the capsule 120. Depending on the material rigidity of the first frame portion 1404, the pressure of the iris 112 against the first frame portion 1404 may urge the second frame portion 1430 to move rearwardly out of the plane P (FIG. 41) in the operative state. FIGS. 42-44 each show some alternate configurations of the refractor 1400', 1400", 1400''', wherein the projections or second frame portions 1430', 1430", 1430''' are shown extending at different angles and both forwardly and rearwardly with respect to the frame 1400', 1400", 1400'''.

The invention claimed is:

1. A surgical apparatus for use in assisting the performance of a procedure on an eye, the eye having a front and rear, a cornea, an iris defining a pupil, and a lens capsule behind the iris, the apparatus comprising:
 a frame having a front and rear, an axis extending in a front-to-rear direction, a first portion and a second portion,
 the first frame portion configured for being operatively connected to the iris, the operatively connected first frame portion extending around the axis and defining a perimeter around an interior area, the first frame portion comprising a plurality of iris engagement surfaces that cooperatively exert a pressure upon an inner edge of the iris around the pupil that maintains the pupil in an enlarged state,
 the second frame portion connected to the first frame portion by at least one support member configured so that at least a part of the second frame portion is maintained by the at least one support member spaced radially inwardly from the first frame portion within the interior area with the first frame portion operatively connected to the iris,
 the part of the second frame portion having a curved edge within the interior area that is concave opening toward the axis to guide movement of a cutting instrument in a curved path along the curved edge with the first frame portion operatively connected to the iris.

2. The surgical apparatus as recited in claim 1 wherein the second frame portion has the form of a plurality of discrete, curved segments that together define the curved edge.

3. The surgical apparatus as recited in claim 1 wherein the first frame portion comprises at least one discrete hinge configured to assist the first frame portion in bending at a predetermined location.

4. The surgical apparatus as recited in claim 1 wherein the second frame portion has a surface with a plurality of spaced indicia configured to assist a measurement of a distance along the curved path.

5. The surgical apparatus as recited in claim 1 wherein the first frame portion generally resides within a plane, and the frame has at least one iris engagement portion that, with the first frame portion operatively connected to an iris, exerts a pressure upon the iris that maintains the pupil in an enlarged state, and the at least one iris engagement portion operatively engages the iris at a location that is spaced from the plane.

6. The surgical apparatus as recited in claim 1 wherein the first frame portion has a channel extending along the perimeter of the first frame portion for accommodating a portion of the iris, the channel bounded by a surface that exerts a pressure upon the iris that maintains the pupil in an enlarged state.

7. The surgical apparatus as recited in claim 1 wherein each of the iris engagement members includes a bend for accommodating a portion of the iris to exert a pressure upon the iris that maintains the pupil in an enlarged state.

8. The surgical apparatus as recited in claim 1 wherein the second frame portion has at least one aperture, the at least one aperture configured to accommodate flow of a fluent substance at a lens capsule with the second frame portion against or adjacent to the lens capsule.

9. The surgical apparatus as recited in claim 1 further comprising at least one capsule engagement member extending from the first frame portion, the at least one capsule engagement member configured to engage a lens capsule with the first frame portion operatively connected to an iris, the at least one capsule engagement member configured to exert a forward pulling force upon the lens capsule as an incident of the first frame portion being operatively connected to the iris.

10. A surgical apparatus for use in assisting the performance of a procedure on an eye, the eye having a front and rear, a cornea, an iris defining a pupil, and a lens capsule behind the iris, the apparatus comprising:
 a frame having a front and rear, an axis extending in a front-to-rear direction, a first portion and a second portion, the first frame portion reconfigurable between a first starting state and a second operative state, the first frame portion having a plurality of sides that extend around the axis and define a perimeter around an interior area with the first frame portion in the second operative state, the first frame portion configured to contact an inner edge portion of an iris with the frame operatively connected to the iris in the second operative state, the second frame portion connected to the first frame portion by at least one support member configured so that at least a part of the second frame portion is maintained by the at least one support member spaced radially inwardly from the first frame portion within the interior area with the first frame portion operatively connected to the iris, the first frame portion operatively connected to the iris and in the second operative state configured to exert a pressure upon an inner edge of the iris to thereby maintain the pupil in an enlarged state, the frame configured so that the second frame portion is urged rearwardly relative to the first frame portion to be supported against the lens capsule as an incident of the first frame portion being changed from the first starting state into the second operative state.

11. The surgical apparatus as recited in claim 10 wherein the second frame portion has a curved edge having a substantially circular shape around the central axis, the curved edge configured to guide movement of an instrument in a curved path with the first frame portion operatively connected to an iris.

12. The surgical apparatus as recited in claim 10 wherein the frame includes at least one capsule engagement member, the at least one capsule engagement member configured to engage a lens capsule with the first frame portion operatively connected to an iris, the at least one capsule engagement member configured to exert a forward pulling force upon the lens capsule as an incident of the first frame portion being operatively connected to the iris and in the second operative state.

13. The surgical apparatus as recited in claim 10 wherein the first frame portion comprises at least one discrete hinge configured to assist the first frame portion in bending at a predetermined location.

14. A method of using a surgical apparatus for assisting the performance of a procedure on an eye, the eye having a front and rear, a cornea, an iris defining a pupil, and a lens capsule behind the iris, the method comprising the steps of:
  a) obtaining a surgical apparatus in accordance with claim 1;
  b) inserting the surgical apparatus through an incision in the cornea; and
  c) operatively engaging the first frame portion with the iris and causing the curved edge to be located proximal to or against the lens capsule.

15. A method of using a surgical apparatus for assisting the performance of a procedure on an eye, the eye having a front and rear, a cornea, an iris defining a pupil, and a lens capsule behind the iris, the method comprising the steps of:
  a) obtaining a surgical apparatus in accordance with claim 10;
  b) inserting the surgical apparatus through an incision in the cornea; and
  c) operatively engaging the first frame portion with the iris and changing the frame first portion from the first starting state into the second operative state to thereby urge the second frame portion rearwardly of the first frame portion.

* * * * *